United States Patent
Zhang

(10) Patent No.: US 10,386,284 B2
(45) Date of Patent: Aug. 20, 2019

(54) DEVICE AND METHOD FOR MEASUREMENT OF DISPERSED OBJECTS USING FLUORESCENT AND NON-FLUORESCENT IMAGING WITH LASER

(71) Applicant: Jianfeng Zhang, Sugar Land, TX (US)

(72) Inventor: Jianfeng Zhang, Sugar Land, TX (US)

( * ) Notice: Subject to any disclaimer, the term of this patent is extended or adjusted under 35 U.S.C. 154(b) by 146 days.

(21) Appl. No.: 15/419,919

(22) Filed: Jan. 30, 2017

(65) Prior Publication Data
US 2017/0219473 A1    Aug. 3, 2017

Related U.S. Application Data

(60) Provisional application No. 62/288,582, filed on Jan. 29, 2016.

(51) Int. Cl.
| | |
|---|---|
| H04N 7/18 | (2006.01) |
| G01N 15/02 | (2006.01) |
| G02B 21/16 | (2006.01) |
| F21V 8/00 | (2006.01) |
| G02B 27/14 | (2006.01) |
| G02B 21/36 | (2006.01) |

(52) U.S. Cl.
CPC ....... *G01N 15/0227* (2013.01); *G02B 6/0005* (2013.01); *G02B 21/16* (2013.01); *G02B 21/367* (2013.01); *G02B 27/141* (2013.01)

(58) Field of Classification Search
CPC .............. G01N 15/0227; G02B 21/367; G02B 27/141; G02B 21/16; G02B 6/0005
USPC .................................................... 348/79–80
See application file for complete search history.

(56) References Cited

U.S. PATENT DOCUMENTS

| | | | |
|---|---|---|---|
| 4,953,978 A | 9/1990 | Bott | |
| 5,159,397 A * | 10/1992 | Kosaka | G01N 15/1427 250/461.2 |
| 5,381,002 A | 1/1995 | Morrow | |
| 5,419,344 A * | 5/1995 | DeWitt | A61B 18/14 128/898 |
| 6,049,381 A * | 4/2000 | Reintjes | G01N 15/0227 356/335 |
| 6,525,325 B1 | 2/2003 | Andrews | |
| 7,248,363 B2 | 7/2007 | Totoki | |
| 7,935,938 B2 | 5/2011 | Thabeth | |
| 8,614,739 B2 * | 12/2013 | Pollack | G06K 9/0014 348/84 |
| 8,809,809 B1 * | 8/2014 | Wu | G02B 21/16 250/458.1 |
| 9,228,898 B2 * | 1/2016 | Kiani | G01J 3/0291 |
| 2013/0300853 A1 * | 11/2013 | Goodwin | G01N 21/6428 348/79 |
| 2015/0198795 A1 * | 7/2015 | Yamauchi | G01N 21/6458 359/385 |

FOREIGN PATENT DOCUMENTS

EP        0997732 A1    5/2000

* cited by examiner

*Primary Examiner* — Anand S Rao
(74) *Attorney, Agent, or Firm* — Ingenium Patents LLC; Peter R. Kramer

(57) ABSTRACT

Measuring devices and methods are described for generating microscopic fluorescence and excitation light images of dispersed objects in liquid or gas, and for analyzing the images to determine the volume fractions of dispersed objects and distinguish different types of objects by comparing the images.

16 Claims, 4 Drawing Sheets

Figure 1:
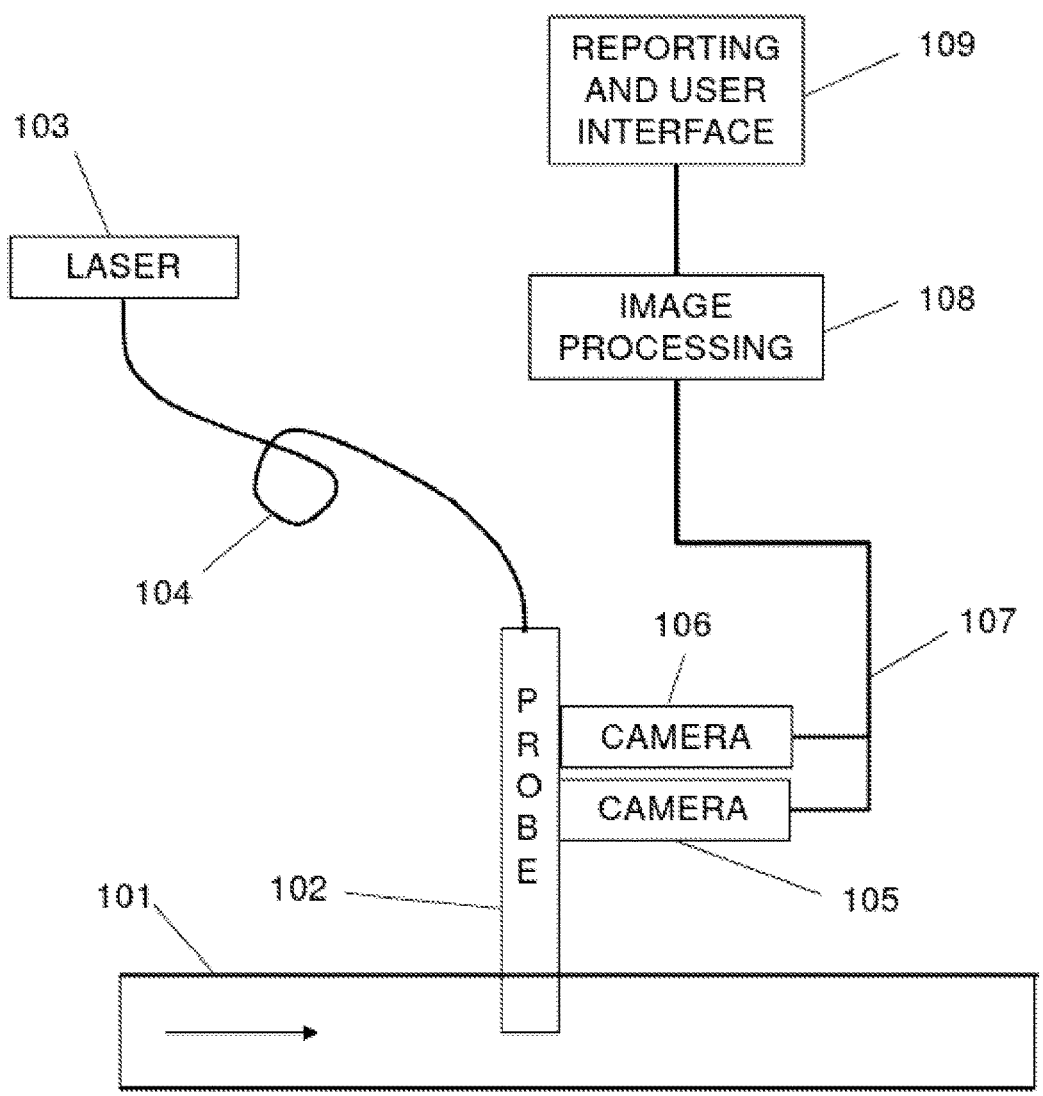

DEVICE AND METHOD FOR MEASUREMENT OF DISPERSED OBJECTS USING FLUORESCENT AND NON-FLUORESCENT IMAGING WITH LASER

CROSS-REFERENCE TO RELATED APPLICATIONS

This application claims priority under 35 USC 119(e) to provisional application No. 62/288,582 which was filed on Jan. 29, 2016.

STATEMENT REGARDING FEDERALLY SPONSORED RESEARCH OR DEVELOPMENT.

The invention is related to federally sponsored research and development under US Department of Energy prime contract number DE-AC26-07NT42677, subcontract 12121-6301-03 entitled "Subsea Produced Water Sensor Development", having subcontract dates Sep. 11, 2014 to Sep. 30, 2016.

BACKGROUND OF THE INVENTION

Field of the Invention

The field of the invention is devices and methods for the measurement of the content of micrometer-scale objects in liquid or gas. Examples of the application include the measurement of oil and solids content in water produced from petroleum and natural gas reservoirs, measurement of oil or other objects in natural gas, detection and quantification of oil in ocean or other bodies of water, detection and quantification of droplets and solids in emissions to air, and measurement of other fluorescent and non-fluorescent microscale dispersed objects.

Description of Related Art Including Information Disclosed Under 37 CFR 1.97 and 1.98.

Measurement of microscale objects carried by fluid are represented by the following patents: U.S. Pat. Nos. 7,935,938 B2, 7,248,363 B2, 6,525,325 B1, European Patent No. EP 0 997 732 A1, U.S. Pat. Nos. 5,381,002, and 4,953,978. in addition, U.S. patent application Ser. No. 14/455,907 describes a system and a method for measuring oil content in water using 3-dimensional laser-induced fluorescence imaging.

BRIEF SUMMARY OF THE INVENTION

The inventor has discovered that the certain types of dispersed material emits fluorescent light under excitation by laser light, which can be used to produce an image with a microscope. The inventor also discovered that the very short duration but high light energy of pulsed laser can be used to eliminate imaging blurring when the dispersed materials moves very fast, for example when the flowing liquid or gas has high velocity. The inventor also discovered that images of the same focal area can be formed with the excitation light, either with the reflected light or transmitted light, and the images can be compared with the fluorescence images to distinguish different types of dispersed objects, some with fluorescence and others without fluorescence. For example, oil droplets, which are fluorescent, can be distinguished from water-wet solid particles and gas bubbles which are not fluorescent. The inventor further discovered that the magnitude of fluorescence of the liquid or gas, which is captured in the fluorescence images, can be utilized to measure the amount of the dissolved materials that cause the fluorescence.

The present invention includes measurement devices and methods for using pulsed laser to produce simultaneous dual modal images, which are fluorescence images and excitation light images, of the objects in a flowing medium which may be liquid or gaseous. The images can be analyzed to determine the volume fractions of dispersed objects and distinguish different types of objects by comparing the images. The invention improves upon the prior art in several areas.

The present invention is a measurement device and method which utilize a pulsed laser to generate microscopic fluorescence and excitation light images of dispersed objects in liquid or gas, and analyze the images to determine the volume fractions of dispersed objects and distinguish different types of objects by comparing the images.

Firstly, the dual modal images greatly enhance the distinguishing of fluorescent objects (such as oil droplets) from non-fluorescent objects (such as solids and gas bubbles), which is important for accurate measurements of the different types of objects.

Secondly, the accuracy of the measurement can be preserved under much higher velocity of liquid or gas when comparing with 2-dimensional imaging methods in prior art. Pulsed lasers can provide sufficient light energy in much shorter pulse width than other types of light source. This can reduce the blurriness of images, and the errors in object volume calculations due to the blurriness, to negligible level even for very high velocity flows. Alternatively, continuous wave lasers can also be used along with cameras with sufficiently high frame rate or sufficiently short shutter time, to achieve the same reduction in image blurriness in high velocity flow situations. The apparatuses and methods disclosed herein can also be applied in situations where it is required for the dispersed objects to keep moving with the flow during the measurement.

BRIEF DESCRIPTION OF THE SEVERAL VIEWS OF THE DRAWING(S)

FIG. 1 A Configuration for Fluorescence and Reflected Excitation Light Images

Figure 2:
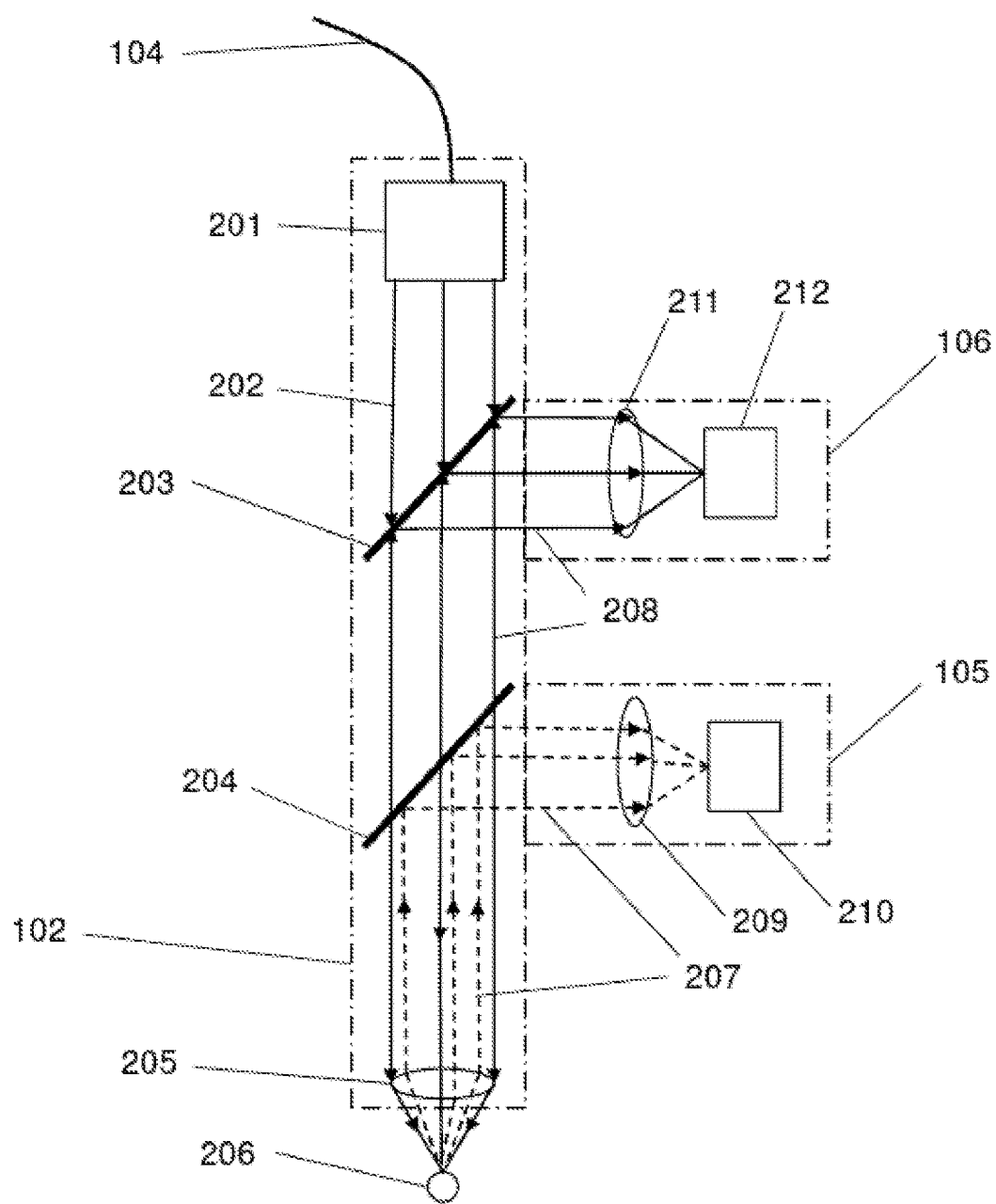
Figure 3:
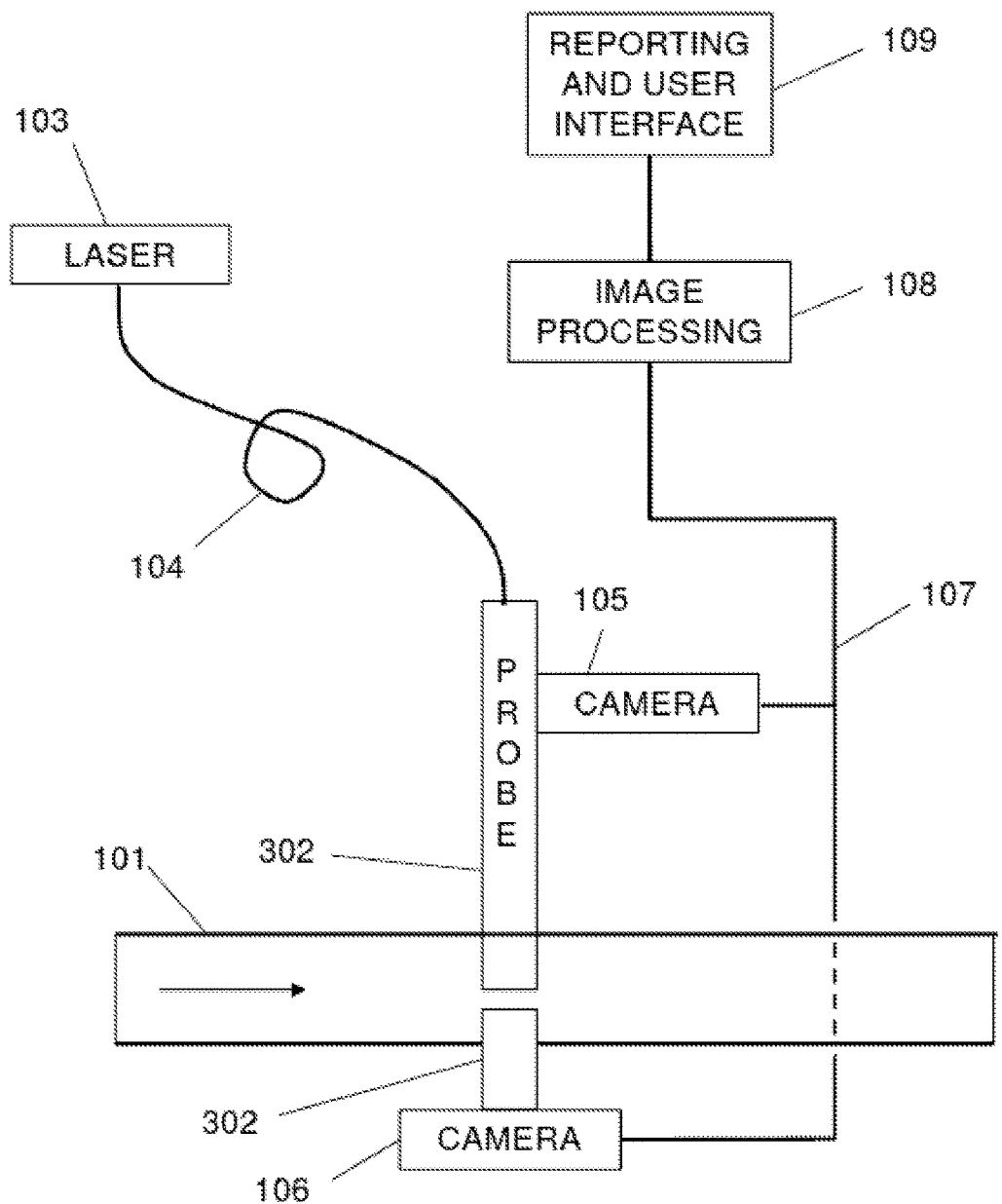
Figure 4:
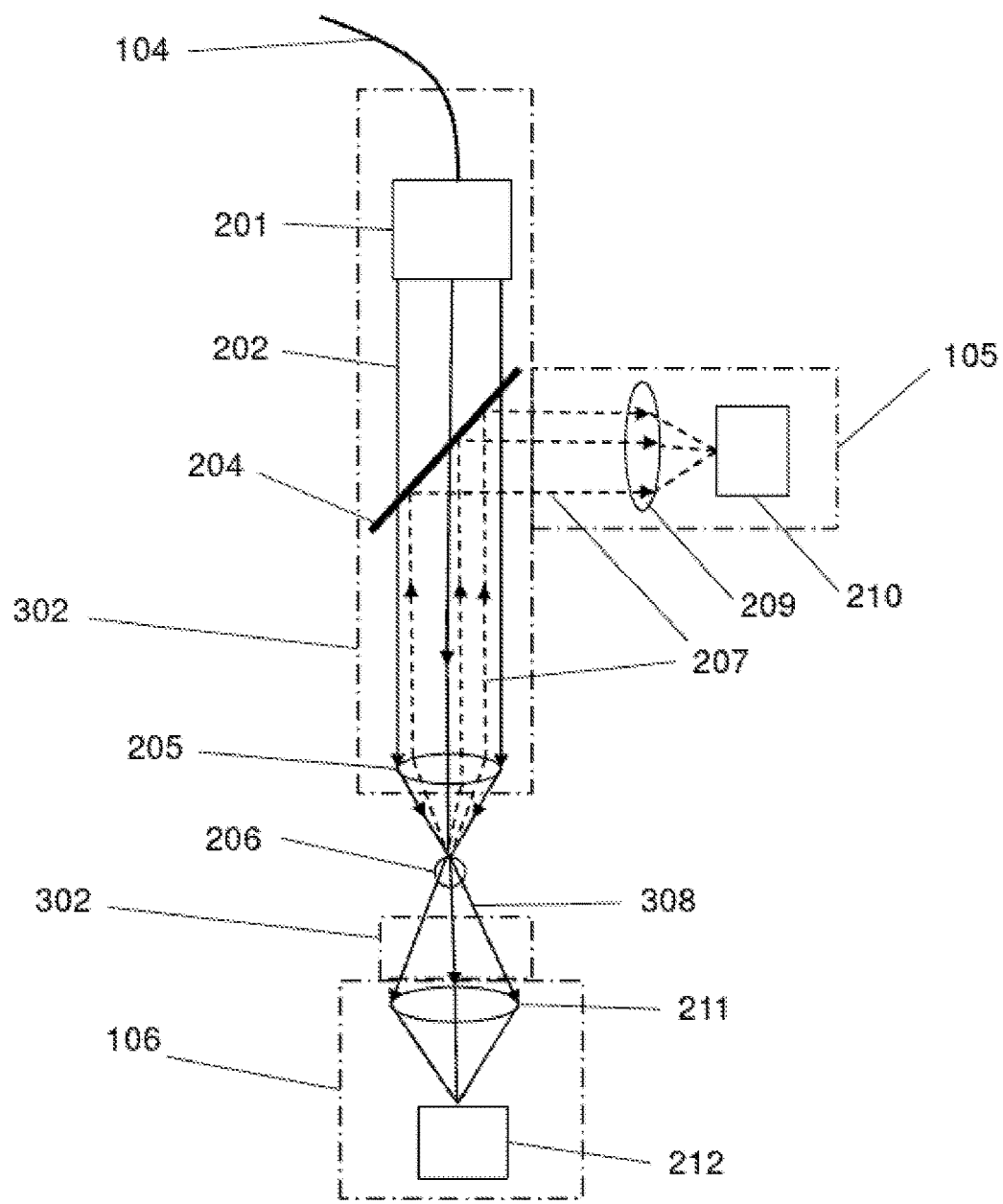

FIG. 2 A configuration such that the excitation light can be used to form transmitted light images FIG. 3 A configuration for taking transmitted excitation fight images simultaneously with the fluorescence images FIG. 4 A configuration for taking transmitted excitation fight images simultaneously with the fluorescence images

REFERENCE NUMERALS USED IN THE SEVERAL VIEWS OF THE DRAWINGS

101 A conduit containing the mixture of the dispersed objects to be measured and the flowing carrier fluid
102 An imaging probe inserted into the mixture (FIG. 1)
103 A laser source
104 A fiber optic cable transmitting the laser from laser source 103 to probe 102
105 A camera capturing images of the dispersed objects with the fluorescence emitted by the objects
106 A camera capturing images of the dispersed objects with the laser light reflected by the objects
107 Power and data cables for controlling the cameras and downloading the images captured
108 An image processing unit, which is a computer at the site or at a remote location 109 A human-machine interface device for the user to control the device and to obtain the measurement results and other information from the device
201 An optical connector and beam expander assembly to prepare the laser light into the appropriate beam size
202 Excitation laser light
203 A beam splitter which both reflects light and transmits light
204 A dichromatic mirror
205 A microscopic objective
206 One of the dispersed objects to be measured
207 Fluorescence light emitted by the object 206
208 Light reflected by the object 206
209 Lens for the fluorescence image camera
210 Sensor to capture the fluorescence image
211 Lens for the excitation light image camera
212 Sensor to capture the excitation light image camera
302 Probe (FIG. 3)
306 Transmitted light (FIG. 4)

DETAILED DESCRIPTION OF THE INVENTION

Configuration For Fluorescence and Reflected Excitation Light Images

A preferred configuration of the device and method is to take fluorescence and reflected excitation light images. The configuration is illustrated in FIG. 1 and FIG. 2. Probe 102 for acquiring images of the objects to be measured is inserted into the pipe 101 which contains liquid or gas flowing in the direction of the arrow. The mixture of the liquid or gas, and the dispersed droplets, are illuminated with pulsed laser from laser source 103. The laser light is also referred to as the excitation light in the description of the present invention. The probe contains a microscopic objective and other optical components for separating the fluorescent light induced by the laser and the reflected excitation light. The images are captured by cameras 105 and 106, analyzed by computer 108 and reported to the user through an interface 109.

Configuration For Fluorescence and Transmitted Excitation Light Images

In an alternative configuration as shown in FIG. 2 probe 302 is configured so that the excitation light can be used to form transmitted light images, which can be analyzed using the same approach as for reflected light images above.

FIGS. 3 and 4 illustrate a configuration for taking transmitted excitation light images simultaneously with the fluorescence images. The configuration is the similar to that for simultaneous fluorescence and reflected excitation light images. Camera 106 is positioned to the side opposite of object 206 with respect to objective 205. Lens 211 focuses transmitted light 308 onto the image sensor 212. The fluorescence images which are captured by camera 105 in this configuration are acquired in essentially the same manner as described for the configuration illustrated in FIG. 2.

Variations of Configuration

The configuration can be varied for different applications without changing the principles of the invention. In one variation, the dispersed objects 205 move in vacuum confined by conduit 101, or in a larger space where probe 102 and 302 are fixed.

In another configuration, the dispersed objects 206 are moved by conveyer belt or other non-flow mechanical devices.

In yet another configuration, the liquid or was carrying the dispersed objects are in a large space not confined by conduit 101. For example, the carrier fluid is ocean water or atmosphere. The device is moved by a vehicle, with the optical end Probe 102 or 302 immersed in the fluid. The concentration of the dispersed objects are measured with the relative motion of the probe and the mixture of the fluid and dispersed objects.

In another configuration, the illumination laser light source is changed to a continuous wave laser. Imaging blurring is prevented by using the cameras with sufficiently high imaging frame rate or sufficiently short shutter time.

The above has disclosed the specifics of the present invention to measure dispersed objects in liquid or gas. It should be apparent to those skilled in the art that many other variations and modifications are possible which are within the spirit of the disclosed invention.

I claim:

1. A measurement device for determining the amount of dispersed objects in a flowing liquid or a flowing gas, distinguishing the types of dispersed objects, and determining the distribution of object sizes, comprising,
    a laser source,
    a probe, said probe further comprising an objective and a dichromatic mirror,
    a fiber optic cable, said fiber optic cable configured to transmit laser light from laser source to said probe,
    a first camera,
    an image processing unit, said image processing unit configured to receive information from said first camera,
    a human machine interface.

2. The measurement device of claim 1 wherein the laser source is a pulsed laser.

3. The measurement device of claim 1 wherein the laser source is a continuous wave laser.

4. The measurement device of claim 2 further comprising a second camera wherein said first camera is positioned to capture fluorescence images and said second camera is positioned to capture excitation light images and said image processing unit configured to receive information from said second camera.

5. The measurement device of claim 4 further comprising a beam splitter, said beam splitter configured to direct excitation light from the liquid or gas to said second camera.

6. The measurement device of claim 4 further comprising a lens configured to focus transmitted excitation light to said second camera.

7. The measurement device of claim 3 further comprising a second camera wherein said first camera is positioned to capture fluorescence images and said second camera is positioned to capture excitation light images and said image processing unit configured to receive information from said second camera.

8. The measurement device of claim 7 further comprising a beam splitter, said beam splitter configured to direct excitation light from the liquid or gas to said second camera.

9. The measurement device of claim 7 further comprising a lens configured to focus transmitted excitation light to said second camera.

10. A method for determining the amount of dispersed objects in a flowing liquid or a flowing gaseous fluid, distinguishing the types of dispersed objects, and determining the distribution of object sizes, comprising,
    illuminating the fluid with a laser light from a laser source,
    capturing fluorescence emissions from the laser illuminated fluid with a first camera, thereby generating fluorescence images, capturing excitation light from the illuminated fluid with a second camera, thereby generating excitation light images, analyzing the fluorescence images and excitation light images with an image processing unit, repeating the sequence of illuminating, capturing, and analyzing steps at a predetermined time interval, statistically analyzing the accumulated results from the repeated illuminating, capturing, and analyzing steps wherein the types of dispersed objects are distinguished and their respective distributions of object sizes determined.

11. The method of claim 10 wherein a pulsed laser illuminates the fluid in the illuminating step.

12. The method of claim 11 wherein the excitation light from the illuminated fluid is captured by the second camera by means of a beam splitter.

13. The method of claim 11 wherein transmitted excitation light from the illuminated fluid is focused through a lens, said lens directing the excitation light to said second camera.

14. The method of claim 10 wherein a continuous wave laser illuminates the fluid in the illuminating step.

15. The method of claim 14 wherein the excitation light from the illuminated fluid is captured by the second camera by means of a beam splitter.

16. The method of claim 15 wherein transmitted excitation light from the illuminated fluid is focused through a lens, said lens directing the excitation light to said second camera.

* * * * *